(12) United States Patent
Detore

(10) Patent No.: US 11,992,641 B2
(45) Date of Patent: May 28, 2024

(54) ELECTRIC TATTOO MACHINE DRIVE

(71) Applicant: Richard Eugene Detore, Edgewater, FL (US)

(72) Inventor: Richard Eugene Detore, Edgewater, FL (US)

( * ) Notice: Subject to any disclaimer, the term of this patent is extended or adjusted under 35 U.S.C. 154(b) by 296 days.

(21) Appl. No.: 17/300,882

(22) Filed: Dec. 8, 2021

(65) Prior Publication Data
US 2023/0173244 A1   Jun. 8, 2023

(51) Int. Cl.
*A61M 37/00*    (2006.01)

(52) U.S. Cl.
CPC .............. *A61M 37/0076* (2013.01)

(58) Field of Classification Search
CPC .................................. A61M 37/0076
USPC ......................................... 335/220
See application file for complete search history.

(56) References Cited

U.S. PATENT DOCUMENTS

| | | | | |
|---|---|---|---|---|
| 2,078,333 | A * | 4/1937 | Lloyd | C10B 1/10 202/218 |
| 7,233,087 | B2 * | 6/2007 | Watson | H02K 53/00 310/75 A |
| 2006/0170302 | A1 * | 8/2006 | Watson | H02K 53/00 310/191 |
| 2018/0323664 | A1 * | 11/2018 | Reddy | H02K 21/042 |

FOREIGN PATENT DOCUMENTS

CN       104702078 A   *   6/2015

* cited by examiner

*Primary Examiner* — Shawki S Ismail
*Assistant Examiner* — Lisa N Homza
(74) *Attorney, Agent, or Firm* — Edward P. Dutkiewicz

(57) ABSTRACT

An electric tattoo machine drive that can be fully controlled electronically using audio technology. An electric tattoo machine drive that can be adjusted hands free or manually by a simple tone generator application on a mobile device. An electric tattoo machine drive able to function in any manner desired by the operator. An electric tattoo machine drive capable of running needle cartridges with a coil machine. A tattoo machine drive able to fit the demands of all users with only one machine. One electric tattoo machine drive to rule them all.

1 Claim, 4 Drawing Sheets

ELECTRIC TATTOO MACHINE DRIVE

BACKGROUND

There are two types of commonly used tattoo machines. A coil machine and a rotary machine. The coil machine is comprised of electromagnets, springs and an armature bar attached to a frame. As a DC current is fed to a coil machine, it engages the magnets pulling down the armature bar and breaking the electric connection turning off the magnets. The springs then force the armature bar back up and the connection is reestablished. Because of its design, a coil machine needs to be tuned to a specific speed, strength and stroke length. This is all changed by the size of coils, the tension of the springs and length and weight of the armature bar along with the use of different compactors. There are thousands of possible set-ups all meant to do different but specific jobs. Because of this an artist has to use 2 or 3 different coil machines for one tattoo. One for outlines, one for shading, etc. . . . . On the other hand, the rotary machine uses a common electric motor to drive a cam that pushes the needle bar. They can only be adjusted by replacing the cam for a different stroke lengths. They can have any number of dampening devices to soften or change the hit strength but the motor itself can only go faster or slower. The amount of current supplied governs this as opposed to a coil machine that stays relatively the same speed but hits harder or softer given a change in the supplied current. The one common ground for both is a DC power supply. Rotary machines do have the advantage of being able to use needle cartridges rather than the more classic separate needle and grip making it possible to easily use one machine for multiple tasks but limited to that machine's stroke length and hit. The nature of a cam drive of a rotary machine also tends to stall at its crest leaving the needle in the skin a little longer than a coil machine making the operation slower for given hertz. As a result there is an industry demand for a machine that hits like a coil machine and is as easy to use as a cartridge style rotary machine while having an adjustable hit, speed and stroke length.

BRIEF SUMMARY OF THE INVENTION

The invention is a magnetic oscillating drive designed to use an audio signal in order to control the functionality of a tattoo machine. The invention makes it possible to have a tattoo machine that can hit harder or softer, faster or slower, with any desired stroke length on demand completely controlled electronically. Utilizing a permanent magnet on a drive bar held in place with spring tension and controlled by one or more electromagnetic coils by means of the oscillating magnetic field produced when fed an audio signal. By using an amplified audio signal rather then a DC current, it is able to oscillate the drive bar and replicate the behavior of any fed signals waveform. It is operated by any common audio tone generator coupled with a common amplifier. As the hertz of the signal is adjusted, the speed of the bar would directly respond. As the amplitude is adjusted the hit would be harder or softer. And by manually adjusting the spring tension the stroke length and overall performance is adjusted. Coupling it with a tone generator mobile device application, it would be possible to make the tattooing procedure machine adjustments hands free making for a much cleaner procedure area. It also will allow us to fully study what waveforms and amplitudes work best making for faster heal times and less permanent undesired scarring and traumatic skin damage. In short, the drive powers a tattoo machine that can act anyway the operator wants it to, eliminating the need to use multiple machines for one tattoo procedure and offering an advanced method for faster, safer and less physically traumatic tattooing experiences.

DETAILED DECRYPTION AND BEST MODE OF IMPLEMENTATION

Figure 1:
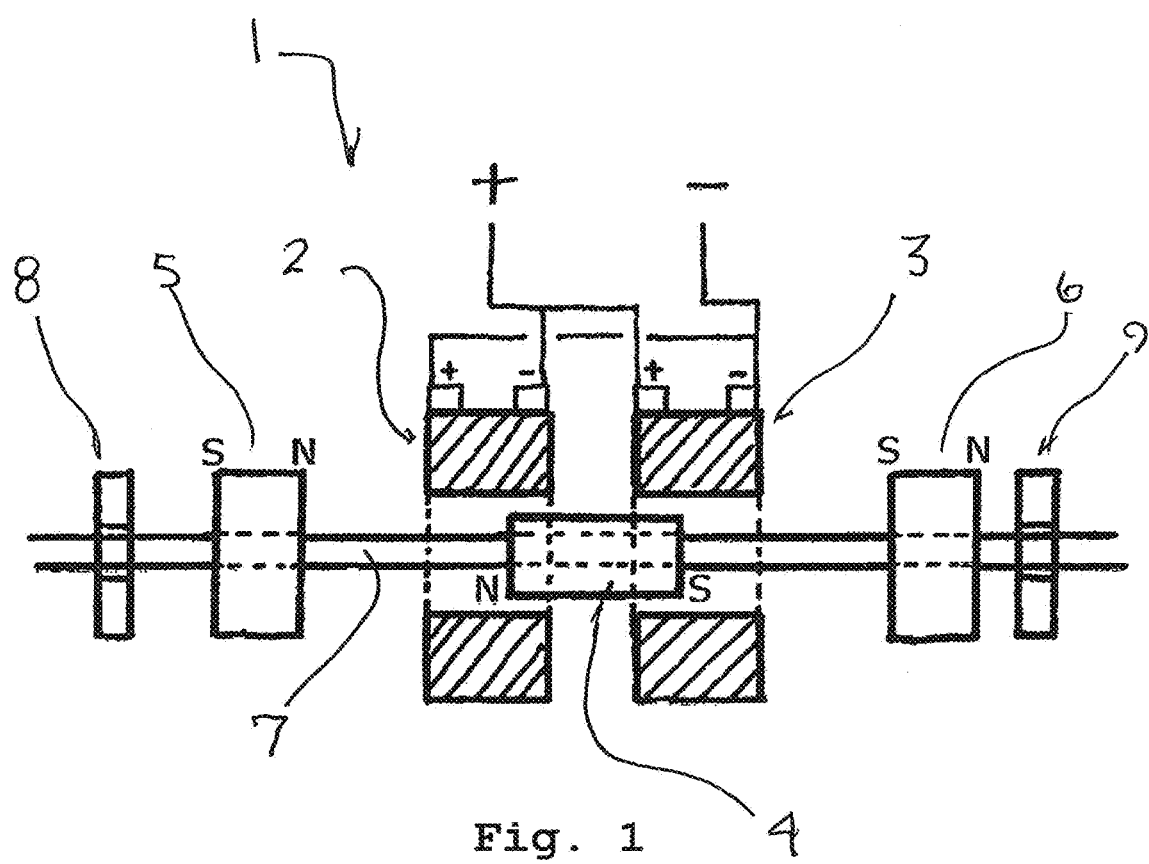
FIG. 1. Shows a cross sectional view of the machine drive utilizing two electromagnet coils wired in parallel with opposing polarity, a magnetic drive core and equally distant check magnets. The drive bar would be held in place using guide bushings attached to any possible number of frame styles.

The invention is simplistic in nature requiring no special circuitry or programing to operate. By only using the force of interacting magnets it is able to follow any frequency signal fed through it. Although it is possible to operate the same basic designs with a controlled DC pulse signal, the positive and negative nature of AC audio waveforms negates the need for any such devices or circuitry that would provide or use such a DC pulse signal. Furthermore, any DC pulse signal would only have a "duty", or on-off cycle and not a full 360' waveform leaving it slave to its spring tension and bar weight during the "off" part of the cycle. So such machine running on such power would still only work well at certain speeds and could never be as efficient. Although the same basic configurations could be used to make DC machine drives, there would be some major internal differences. The coil on the audio drive would need to replicate the resistance of a speaker. Amplifiers are rated for speakers with a certain amount of ohms resistance. The coil itself would need to be the same in order to keep the amp from dumping too much power and overheating. An inline resistor could also help compensate for some of this. DC coils for DC tattoo machine drives have a much lower resistance and would not work properly using an amplified audio signal. They would quickly over-heat and fail. And most of the common DC power supplies do not have enough power to push a coil designed for audio. The spring tension would also be completely different. The Audio drive would have much more spring tension than a DC drive. Lastly an AC/audio signal offers the full wave cycle that keeps the drive bar in full control at all times. In the same way a speaker works where a coil is fed a signal making it react with the permanent magnet to move the voice cone in and out, when the positive and negative waves come thus sound is produced, this is able to move the attached shaft or drive bar in and out pushing and pulling any given needle or tool.

This makes a boosted audio signal the perfect solution for controlling any oscillating machine that can be powered from the standard wattages of common amplifiers.

There are three basic elements to the operation of my preferred configuration. A tone generator, an amplifier and a tattoo machine using the invention as its drive. For example, if an artist wanted to start a tattoo after preparing everything they would simply pick what type waveform they want to use, i.e. square wave or sine wave, etc. . . . and what frequency on the tone generator; then set the amplification to the desired hardness of hit and get to work. Then, when the lines are finished and it's time to shade, they can simply reset those parameters to achieve their desired reaction from the drive. Let's say that is 100 cycles per second. Once the hertz are set to 100 on the tone generator it would be sending one positive and one negative signal back to back at a time a hundred times a second. Every time there was a positive wave the electro magnets would polarize one direction and then reverse their polarity when the negative wave came. By nature, the magnetic core would respond most unpredictable and erratically without another outside force to hold it in the oscillating magnetic field's sweet spot. It uses spring tension in order to solve this problem. By holding the drive bar magnets in the sweet spot and allowing fine-tuning of overall performance. This could be done with any type of metal springs, rubber or synthetic baffles or permanent magnets with opposing polarity.

Figure 2:
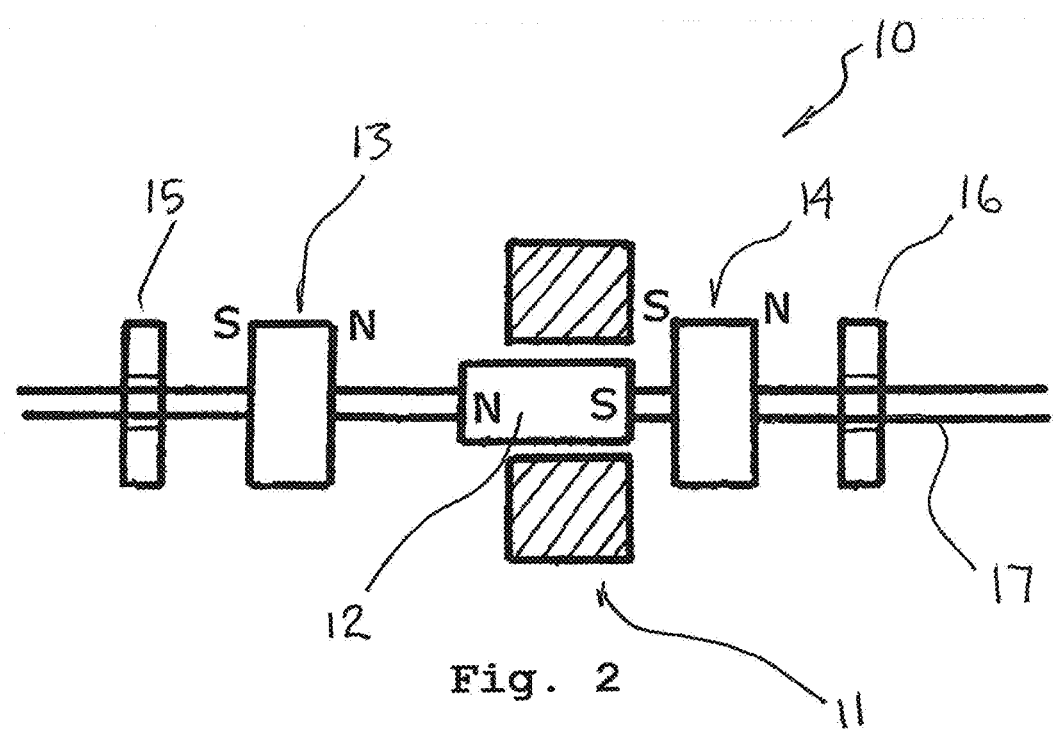
FIG. 2. Uses another cross sectional view to illustrate another possible configuration of the invention utilizing only one electromagnetic coil, a magnetic drive core and two strategically placed check magnets. Otherwise FIG. 2 operates on the same principles as FIG. 1
Figure 3:
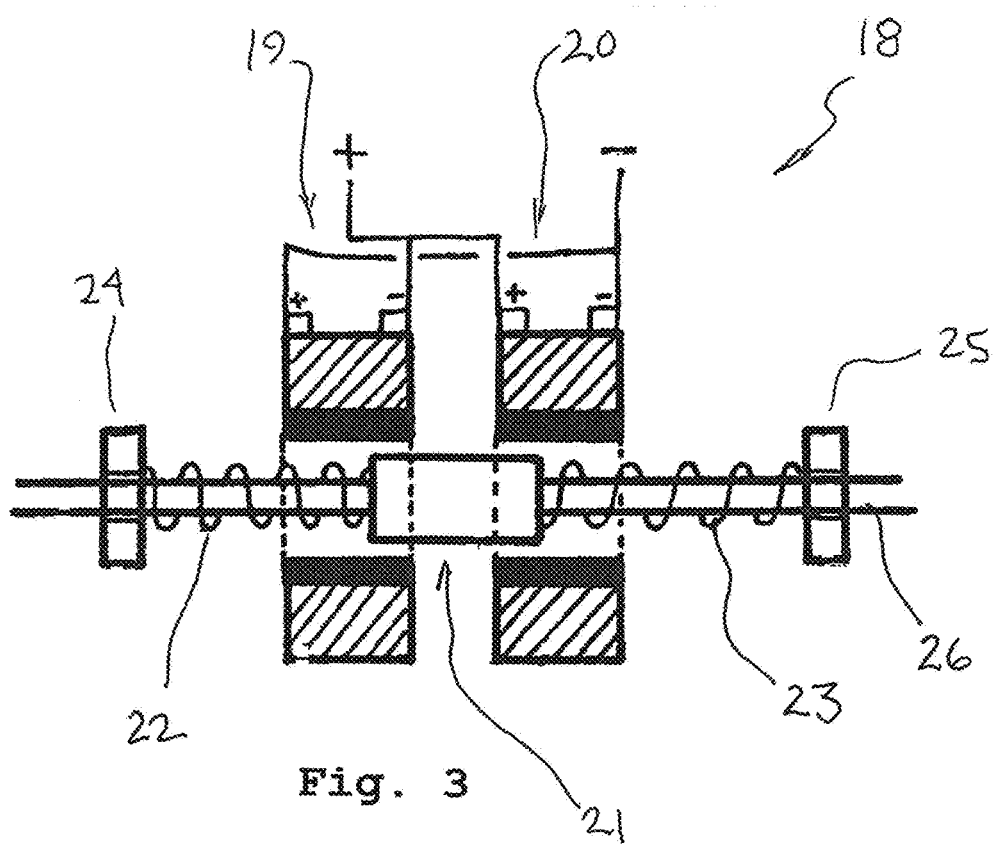
FIG. 3. Shows yet another cross sectional possible configuration utilizing two electromagnetic coils with fixed ferromagnetic cores, an iron drive core and metal coil springs. This configuration could also be affixed to any number or style of drive housing frames.
Figure 4:
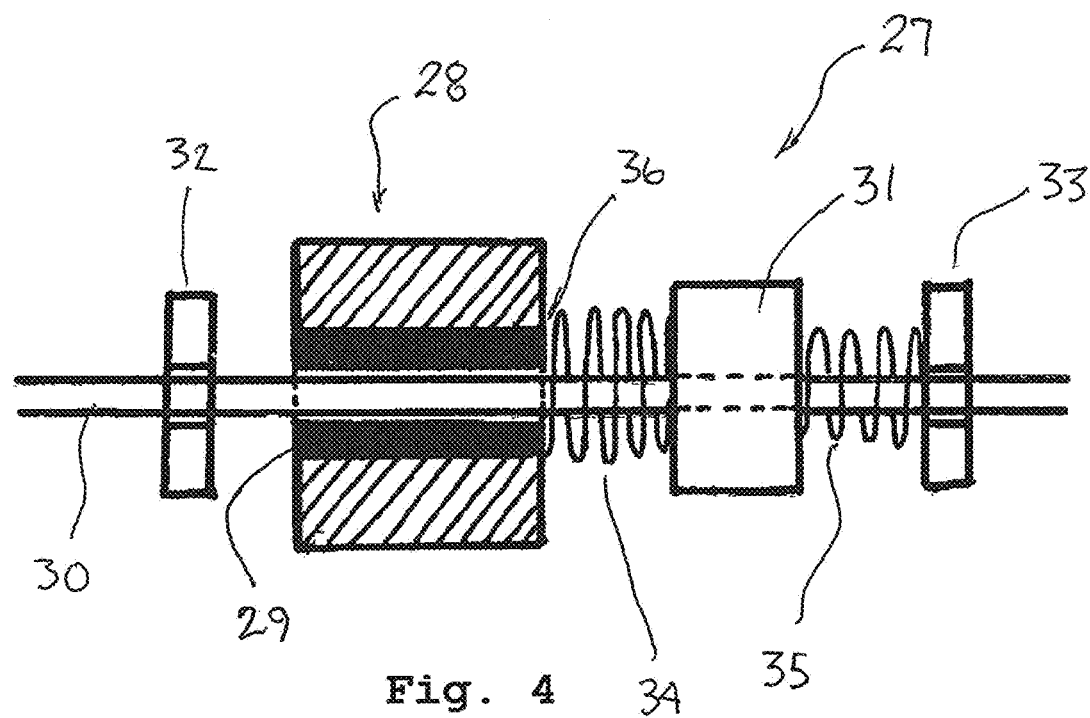
FIG. 4. Shows the cross sectional configuration of the preferred drive developed through experimentation and is the current working drive in testing. It utilizes a single coil with a fixed ferromagnetic core, a magnetic drive bar and metal coil springs.

There are numerous possible configurations to which this could be achieved. The one thing they all have in common is that they use an electromagnetic coil to control the movement of a permanent magnet with the assistance of spring tension to keep them in the oscillating magnetic fields sweet spot. These drives could be fixed to any infinite number of frame styles. After many hours and days and weeks of testing I have found that a combination of FIG. 2 and FIG. 3 to be the most efficient platform, hence FIG. 4. During early testing I learned that two coils tend to create a phase issue. Using one coil solved this issue. I also learned that check magnets do not offer the degree of fine-tunability that can be achieved with metal coil springs for the spring tension with the commercially available products. Though I do think in the future magnets still offer a possible upgrade to the drive. For now it is out of my scope.

In (FIG. 1) we see a drive core magnet attached to a drive bar. At either end the bar would ride through the check magnets then into guide bushings. The bushings will keep the drive core magnet from touching the sides while the check magnets keep the core magnet horizontally centered. There are two coils built on the drive housing with a small gap between them. This gap will play a big part in how the core magnet responds and is being tested. I have found that if they are too close together it creates some distortion in the field. The two coils are wired to be polar opposite meaning when one charges with a positive pulse the other is negative. Thus creating a controlled oscillating magnetic field that the drive core magnet will directly respond to.

In (FIG. 2.) the only major difference from (FIG. 1.) is having one coil instead of two. This configuration wound need off-center check magnets to keep the drive core magnet on the desired side of the electromagnetic coil. Otherwise it operates on the same principles as (FIG. 1.)

In (FIG. 3.) we see a drive bar attached to a soft iron drive core. Coil springs replace the check magnets and iron sleeve cores are added to the electromagnet coils. Without the iron coil sleeve cores the electromagnets would not have sufficient power to control the drive core. Otherwise it also works on the same principles.

In (FIG. 4.) we see a single ferromagnetic core based electromagnetic coil with permanent magnets on a drive bar off to one side. The drive bar magnets are held in the magnetic fields sweet spot with two coil springs. The outside coil spring is adjustable in order to tune the drive. The bar would ride in bushings on the ends.

On top of being able to change the hertz/speed, amplitude/hit and stroke length, the invention will also respond differently depending on the type of signal or waveform it is fed. In my early testing, a square wave is a harder hit and a sine wave is softer. This will give us the ability to fully understand what signals will be the least damaging to the skin and most efficient. It will also allow us to replicate any type of tattoo machine in existence by studying its strike signature or the movement cycle it produces. We will be able to create a simple tone generator application with specific parameters to run the drive giving us the ability to run the drive hands free using any phone, pad or tablet device. This makes for a much cleaner procedure environment. Whether it is a tattoo studio or a doctors office anything that minimizes cross-contamination is extremely desired. The application will be able to have presets, be able to chose different types of waveforms, turn up or down the amplitude and turn up or down the hertz, all by either using voice commands or manually. The application would only need to be plugged into a small amplifier via headphone jack or bluetooth that is set to the proper amplification.

What is claimed as being new and desired to be protected by LETTERS PATENT of the United States is as follows:

1. An electric tattoo machine comprising:
   a tattoo machine drive being powered by and controlled by an alternating current audio signal:
   an electromagnetic coil being operatively coupled to an audio signal, the electromagnetic coil generating an oscillating electromagnetic field, the electromagnet having a fixed ferromagnetic core, the electromagnetic coil having a passageway there through;
   a drive bar having an attached permanent magnet, the permanent magnet interacting with the electromagnets oscillating magnetic field, the drive bar permanent magnet being located outside of the electromagnetic coil passageway;
   the drive bar having a pair of associated metal coil springs, the pair of metal coil springs holding the drive bar magnet in the oscillating magnetic field;
   the drive bar attached permanent magnet being located between the pair of drive bar associated metal coil springs, the drive bar attached permanent magnet being located outside of the electromagnetic coil passageway; and
   a pair of opposed guide bushings, the drive bar moving through the guide bushings.

* * * * *